(12) United States Patent
Marmorstein et al.

(10) Patent No.: US 8,180,580 B2
(45) Date of Patent: May 15, 2012

(54) METHOD FOR IDENTIFYING A COMPOUND THAT MODULATES SIR2 PROTEIN ACTIVITY

(75) Inventors: Ronen Marmorstein, Swarthmore, PA (US); Brandi D. Sanders, Pittman, NJ (US)

(73) Assignee: The Wistar Institute, Philadelphia, PA (US)

( * ) Notice: Subject to any disclaimer, the term of this patent is extended or adjusted under 35 U.S.C. 154(b) by 419 days.

(21) Appl. No.: 12/023,287

(22) Filed: Jan. 31, 2008

(65) Prior Publication Data

US 2008/0305496 A1     Dec. 11, 2008

Related U.S. Application Data

(60) Provisional application No. 60/887,642, filed on Feb. 1, 2007.

(51) Int. Cl.
    *G01N 31/00*     (2006.01)
    *G06G 7/58*     (2006.01)
    *C12Q 1/34*     (2006.01)
    *C12N 9/78*     (2006.01)

(52) U.S. Cl. ............... 702/27; 703/11; 435/18; 435/227

(58) Field of Classification Search .................. None
See application file for complete search history.

(56) References Cited

U.S. PATENT DOCUMENTS

2004/0137518 A1*   7/2004   Lambert et al. ................. 435/7.1
2005/0267023 A1*   12/2005   Sinclair et al. .................... 514/12
2006/0025337 A1   2/2006   Sinclair et al.

OTHER PUBLICATIONS

Grozinger et al., J. Biol. Chem. 276:38837-38843, 2001.*
Flower, "Drug Design, Cutting Edge Approaches," Royal Society of Chemistry, Cambridge, UK, 2002, pp. 21-27.*
PBD Id: 1SZD—Feb. 2004.
PBD Id: 1SZC—Apr. 2004.
Avalos et al., "Mechanism of Sirtuin Inhibition by Nicotinamide:Altering the Nad+ Cosubstrate Specificity of a Sir2 Enzyme", Molecular Cell 2005 17:855-868.
Avalos et al., "Structural Basis for the Mechanism and Regulation of Sir2 Enzymes", Molecular Cell 2004 13:639-648.
Chang et al., "Structural Basis for the NAD-dependent Deacetylase Mechanism of Sir2", J. Biol. Chem. 2002 277(37):34489-34498.
Min et al., "Crystal Structure of a SIR2 Homolog-NAD Complex", Cell 2001 105:269-279.
Slama et al., "Carbanicotinamide Adenine Dinucleotide : Synthesis and Enzymological Properties of a Carbocyclic Analogue of Oxidized Nicotinamide Adenine Dinucleotide", Biochemistry 1988 27:183-193.
Slama et al., "Inhibition of NAD Glycohydrolase and ADP-ribosyl Transferases by Carbocyclic Analogues of Oxidized Nicotinamide Adenine Dinucleotide", Biochemistry 1989 28:7688-7694.
Zhao et al., "Structure of the Yeast Hst2 Protein Deacetylase in Ternary Complex with 2'-O-Acetyl ADP Ribose and Histone Peptide", Structure 2003 11:1403-1411.
Zhao et al., "Structural basis for nicotinamide cleavage and ADP-ribose transfer by NAD+-dependent Sir2 histone/protein deacetylases", Proc. Natl. Acad. Sci. USA 2004 101(23):8563-8568.
Mai et al., "Design, Synthesis, and Biological Evaluation of Sirtinol Analogues as Class III Histone/Protein Deacetylase (Sirtuin) Inhibitors", J. Med. Chem. 2005 48:7780-7795.

* cited by examiner

*Primary Examiner* — David J Steadman
(74) *Attorney, Agent, or Firm* — Licata & Tyrrell P.C.

(57) ABSTRACT

The present invention relates to a method for identifying compounds that modulate the activity of sirtuin deacetylase protein family members. Compounds of the invention are identified by designing or screening for a compound which binds to at least one amino acid residue of the newly identified nicotinamide inhibition and base exchange site of Sir2 and testing the compound for its ability to modulate the activity of the Sir2 protein. Compositions and methods for preventing or treating diseases or disorders associated with Sir2 are also provided.

1 Claim, 3 Drawing Sheets

SEQUENCE LISTING

<160> NUMBER OF SEQ ID NOS: 1

<210> SEQ ID NO 1
<211> LENGTH: 357
<212> TYPE: PRT
<213> ORGANISM: Saccharomyces cerevisiae

<400> SEQUENCE: 1

```
Met Ser Val Ser Thr Ala Ser Thr Glu Met Ser Val Arg Lys Ile Ala
1               5                   10                  15

Ala His Met Lys Ser Asn Pro Asn Ala Lys Val Ile Phe Met Val Gly
                20                  25                  30

Ala Gly Ile Ser Thr Ser Cys Gly Ile Pro Asp Phe Arg Ser Pro Gly
            35                  40                  45

Thr Gly Leu Tyr His Asn Leu Ala Arg Leu Lys Leu Pro Tyr Pro Glu
        50                  55                  60

Ala Val Phe Asp Val Asp Phe Phe Gln Ser Asp Pro Leu Pro Phe Tyr
65                  70                  75                  80

Thr Leu Ala Lys Glu Leu Tyr Pro Gly Asn Phe Arg Pro Ser Lys Phe
                85                  90                  95

His Tyr Leu Leu Lys Leu Phe Gln Asp Lys Asp Val Leu Lys Arg Val
            100                 105                 110

Tyr Thr Gln Asn Ile Asp Thr Leu Glu Arg Gln Ala Gly Val Lys Asp
        115                 120                 125

Asp Leu Ile Ile Glu Ala His Gly Ser Phe Ala His Cys His Cys Ile
130                 135                 140

Gly Cys Gly Lys Val Tyr Pro Pro Gln Val Phe Lys Ser Lys Leu Ala
145                 150                 155                 160

Glu His Pro Ile Lys Asp Phe Val Lys Cys Asp Val Cys Gly Glu Leu
                165                 170                 175

Val Lys Pro Ala Ile Val Phe Phe Gly Glu Asp Leu Pro Asp Ser Phe
            180                 185                 190

Ser Glu Thr Trp Leu Asn Asp Ser Glu Trp Leu Arg Glu Lys Ile Thr
        195                 200                 205

Thr Ser Gly Lys His Pro Gln Gln Pro Leu Val Ile Val Val Gly Thr
210                 215                 220

Ser Leu Ala Val Tyr Pro Phe Ala Ser Leu Pro Glu Glu Ile Pro Arg
225                 230                 235                 240

Lys Val Lys Arg Val Leu Cys Asn Leu Glu Thr Val Gly Asp Phe Lys
                245                 250                 255

Ala Asn Lys Arg Pro Thr Asp Leu Ile Val His Gln Tyr Ser Asp Glu
            260                 265                 270

Phe Ala Glu Gln Leu Val Glu Glu Leu Gly Trp Gln Glu Asp Phe Glu
        275                 280                 285

Lys Ile Leu Thr Ala Gln Gly Gly Met Gly Asp Asn Ser Lys Glu Gln
290                 295                 300

Leu Leu Glu Ile Val His Asp Leu Glu Asn Leu Ser Leu Asp Gln Ser
305                 310                 315                 320

Glu His Glu Ser Ala Asp Lys Lys Asp Lys Lys Leu Gln Arg Leu Asn
                325                 330                 335

Gly His Asp Ser Asp Glu Asp Gly Ala Ser Asn Ser Ser Ser Ser Gln
            340                 345                 350

Lys Ala Ala Lys Glu
        355
```

METHOD FOR IDENTIFYING A COMPOUND THAT MODULATES SIR2 PROTEIN ACTIVITY

This application claims benefit of priority to U.S. Provisional Patent Application Ser. No. 60/887,642, filed Feb. 1, 2007, the content of which is incorporated herein by reference in its entirety.

This invention was made in the course of research sponsored by the National Institutes of Health (NIH Grant Nos. CA107107, CA09171, RR-01646) and the National Science Foundation (NSF Grant No. DMR 0225180). The government has certain rights in the invention.

BACKGROUND OF THE INVENTION

The class III family of histone deacetylases, silent information regulator 2 (Sir2) proteins, require $NAD^+$ to remove an acetyl moiety from the ε-amino group of lysine residues within protein targets (Imai, et al. (2000) *Nature* 403:795-800; Landry, et al. (2000) *Proc. Natl. Acad. Sci. USA* 97:5807-5811; Smith, et al. (2000) *Proc. Natl. Acad. Sci. USA* 97:6658-6663) to yield the deacetylated protein target, nicotinamide, and 2'-O-acetyl-ADP-ribose (Jackson and Denu (2002) *J. Biol. Chem.* 277:18535-18544; Sauve, et al. (2001) *Biochemistry* 40:15456-15463). Sir2 proteins are broadly conserved from bacteria to humans (Brachmann, et al. (1995) *Genes Dev.* 9:2888-2902), and they are able to deacetylate numerous proteins in addition to histones, including acetyl-coA synthetase (Starai, et al. (2002) *Science* 298:2390-2392), α-tubulin (North, et al. (2003) *Mol. Cell.* 11:437-444), myoD (Fulco, et al. (2003) *Mol. Cell* 12:51-62), p53, FOXO, Ku70, and NF-κB (Longo and Kennedy (2006) *Cell* 126:257-268). Their ability to deacetylate such a wide range of substrates has implicated them in playing a stimulatory role in a wide spectrum of biological functions including DNA recombination (Gottlieb and Esposito (1989) *Cell* 56:771-776) and repair (Bennett, et al. (2001) *Mol. Cell. Biol.* 21:5359-5373), longevity, transcriptional silencing, apoptosis, axonal protection, insulin signaling and fat mobilization (Longo and Kennedy (2006) supra). In addition, increased dosage or expression of Sir2 has been shown to increase lifespan in yeast, worms, flies, and mice, and increased longevity due to a calorie-restricted diet has been shown in most of these animals to be Sir2 dependant (Longo and Kennedy (2006) supra). Conversely, decreased Sir2 activity due to gene deletion or enzyme inhibition shortens yeast lifespan (Kaeberlein, et al. (1999) *Genes Dev.* 13:2570-2580). Deletion of the mammalian SIRT6 homologue in mice results in genomic instability and an aging-like phenotype (Mostoslavsky, et al. (2006) *Cell* 124:315-329).

Sir2 proteins couple the removal of the acetyl moiety of acetyl-lysine to cleavage of the high energy glycosidic bond between nicotinamide and ADP-ribose in β-$NAD^+$. Nicotinamide, a reaction product and noncompetitive inhibitor of Sir2 proteins (Bitterman, et al. (2002) *J. Biol. Chem.* 277:45099-45107; Landry, et al. (2000) supra), has also been shown to be a physiological regulator of this family of proteins (Schmidt, et al. (2004) *J. Biol. Chem.* 279:40122-40129). Yeast cells grown in the presence of nicotinamide show a dramatic reduction in silencing, an increase in rDNA recombination, and a shortening of replicative lifespan (Bitterman, et al. (2002) supra). Nicotinamide can also inhibit Sir2 deacetylation of p53 in mouse embryonic fibroblast cells upon DNA damage (Luo, et al. (2001) *Cell* 107:137-148), and of histones H3 and H4 in human embryonic kidney cells, which leads to loss of repression by COUP transcription factor interacting proteins 1 and 2 (Senawong, et al. (2003) *J. Biol. Chem.* 278:43041-43050). Depletion of nicotinamide by overexpression of PCN1, a gene that encodes a nicotinamide deaminase, is sufficient to activate Sir2 and extend yeast lifespan (Anderson, et al. (2003) *Nature* 423:181-185; Gallo, et al. (2004) *Mol. Cell. Biol.* 24:1301-1312).

Structural studies of the catalytic core region of Sir2 homologues reveal a large and conserved Rossmann fold domain, a smaller and more structurally diverse zinc binding domain, and a series of loops connecting the two domains, forming the catalytic cleft where the substrates bind (Min, et al. (2001) *Cell* 105:269-279). Several structures of Sir2 proteins in complex with $NAD^+$ in a nonproductive conformation (Avalos, et al. (2004) *Mol. Cell* 13:639-648; Chang, et al. (2002) *J. Biol. Chem.* 277:34489-34498; Min, et al. (2001) supra; Zhao, et al. (2003) *Structure* 11:1403-1411) make clear that simultaneous acetyl-lysine binding is required for $NAD^+$ to adopt a productive conformation where it is catalytically competent (Avalos, et al. (2004) supra; Zhao, et al. (2004) *Proc. Natl. Acad. Sci. USA* 101:8563-8568). In this productive conformation, the nicotinamide group of $NAD^+$ is bound in a highly conserved "C pocket" (Min, et al. (2001) supra). Furthermore, structures of *A. fulgidus* Sir2-Af2 bound to $NAD^+$ or ADP-ribose and *Thermotoga maritima* SirTm bound to acetyl-lysine in the presence of high concentrations of nicotinamide show nicotinamide bound in the highly conserved C pocket (Avalos, et al. (2005) *Mol. Cell.* 17:855-868). While an alternate pocket, distinct from the "C pocket", has been suggested for binding the inhibitory nicotinamide molecule (Zhao, et al. (2004) supra), the nature of this site was not provided.

Compounds which modulate the activity of sirtuin deacetylase protein family members are disclosed in U.S. Patent Application No. 20060025337. While these compounds activate Sir2 enzymes, they do not reverse the $V_{max}$ decrease associated with nicotinamide.

Needed in the art are compounds that can relieve or enhance the inhibition of Sir2 proteins by nicotinamide. The present invention meets this need in the art by providing the nicotinamide inhibition and base exchange site of Sir2 for use as a target for identifying Sir2 protein effectors.

SUMMARY OF THE INVENTION

The present invention is a method for identifying a compound which modulates the activity of a silent information regulator 2 (Sir2) protein. The method involves the steps of a) designing or screening for a compound which binds to at least one amino acid residue of the nicotinamide inhibition and base exchange site of Sir2, and b) testing the compound designed or screened for in (a) for its ability to modulate the activity of the Sir2 protein, thereby identifying a compound that modulates the activity of a Sir2 protein. In one embodiment, the nicotinamide inhibition and base exchange site of Sir2 is formed by the amino acid residues set forth in Table 1. In another embodiment, the nicotinamide inhibition and base exchange site of Sir2 is formed by amino acid residues 44, 64, 67, 116, 117 and 184 of SEQ ID NO:1. In a still further embodiment, screening is carried out in the presence of nicotinamide so that a selective Sir2 activator is identified. Compounds identified by the methods of the present invention are also provided as are methods of using such compounds for modulating Sir2 activity and in the prevention or treatment of diseases or conditions involving Sir2 protein.

BRIEF DESCRIPTION OF THE DRAWINGS

FIG. 1 shows the activity, kinetic, and inhibition data for wild-type and mutant yHst2.

DETAILED DESCRIPTION OF THE INVENTION

Figure 1A:
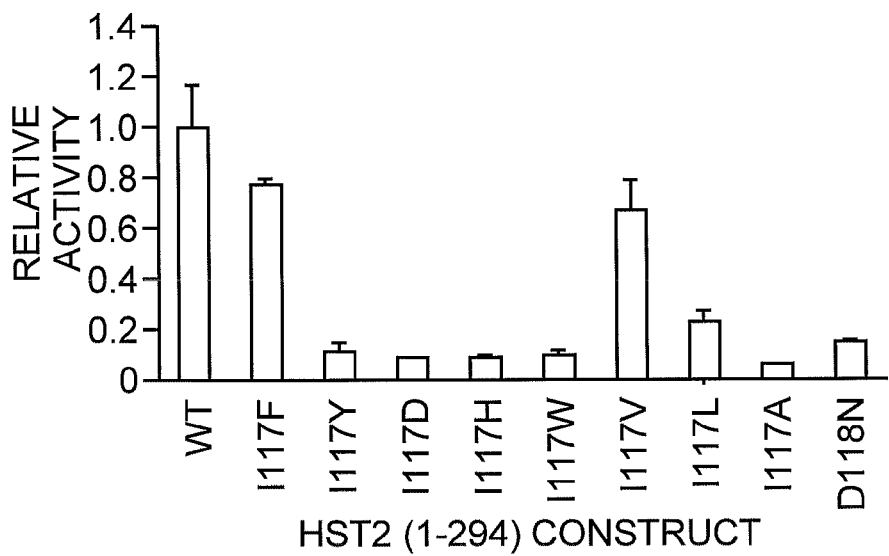
FIG. 1A shows the relative activity of wild-type and mutant yHst2 enzymes based on their ability to deacetylate a fluorescently-labeled acetylated peptide in duplicate. Error bars represent one SD of experiments done at least in triplicate.

The nicotinamide inhibition and base exchange site of Sir2 enzymes has now been identified. Biochemical studies and structural analysis indicate that this site is distinct from the C pocket binding site for the nicotinamide group of NAD$^+$ and is physiologically relevant for nicotinamide regulation of sirtuins. Given the identification of this new regulatory site, compounds can now be designed or screened that specifically target this site and modulate the activity Sir2 proteins.

By way of illustration, the nicotinamide inhibition and base exchange site of Sir2 was determined for the Sir2 homologue, yeast Hst2, the amino acid sequence of which is set forth herein as SEQ ID NO:1. Based upon the crystal structure analysis of yHst2 in complex with an acetyl-lysine 16 histone H4 peptide, intermediate analogue ADP-HPD, and nicotinamide, the nicotinamide inhibition and base exchange site of Sir2 was identified as a hydrophobic pocket formed by amino acid residues F44, E64, F67, N116, I1117, and F184. The location of these residues in yHst2 and homologues of yHst2 are listed in Table 1.

TABLE 1

| Source | Sir2 | GENBANK Accession No. | Corresponding Amino Acid Residue in Reference Sequence | | | | | |
|---|---|---|---|---|---|---|---|---|
| | | | F44 | E64 | F67 | N116 | I117 | F184 |
| S.c. | yHst2 | NP_015310 | F44 | E64 | F67 | N116 | I117 | F184 |
| D.m. | dSir2 | NP_477351 | F241 | Q262 | F265 | N314 | I315 | F401 |
| H.s | SirT1 | NP_036370 | F273 | Q294 | F297 | N346 | I347 | F414 |
| | SirT2 | AAK51133 | F59 | E79 | F82 | N131 | I132 | F198 |
| | SirT3 | NP_036371 | F157 | E177 | F180 | N129 | I130 | F294 |
| M.m. | SirT1 | NP_062786 | F265 | Q286 | F289 | N338 | I339 | F406 |
| | SirT3 | AAH25878 | F15 | E35 | F38 | N87 | I88 | F152 |
| C.f. | Sir2 | AAZ81418 | F60 | E80 | F83 | N132 | I133 | F199 |
| R.n. | Sir2 | NP_001008369 | F59 | E79 | F82 | N131 | I132 | F198 |

S.c., *Saccharomyces cerevisiae*;
D.m., *Drosophila melanogaster*;
H.s., *Home sapiens*;
M.m., *Mus musculus*;
C.f., *Canis familiaris*;
R.n., *Rattus norvegicus*.

A Sir2 enzyme or protein of the present invention is intended to include any member of the silent information regulator 2 family of proteins which transfers an ADP-ribose group from NAD$^+$ to an acetyl group (or a protein carrier as is the case with a subset of Sir2 proteins) (Frye (1999) *Biochem. Biophys. Res. Commun.* 260:273-279). As such, a Sir2 protein can be from any source (see, e.g., Sir2 proteins listed in Table 1). A Sir2 protein of the invention can be identified by the presence of the conserved motif Cys-Xaa-Xaa-Cys-(Xaa)$_{15-20}$-Cys-Xaa-Xaa-Cys SEQ ID NO:2), which binds to Zn$^+$ ions (Min, et al. (2001) supra). Molecular phylogenetic analysis has shown that eukaryotic Sir2-like proteins can be grouped into four main branches designated classes I-IV (Frye (2000) *Biochem. Biophys. Res. Commun.* 273:793-98). For example, the seven human sirtuin genes include all four classes: SIRT1, SIRT2, and SIRT3 are class I, SIRT4 is class II, SIRT5 is class III, and SIRT6 and SIRT7 are class IV. In particular embodiments, the Sir2 protein is a class I eukaryotic Sir2.

Because of the involvement of Sir2 proteins in a growing number of cellular processes, Sir2 proteins are therapeutic drug targets for the development of small molecule effectors. The information obtained from the inhibitor-bound Sir2 complex crystal structures of the present invention reveal detailed information which is useful in the design, isolation, screening and determination of potential compounds which modulate the activity of Sir2 family members. Compounds that bind in the nicotinamide binding site, D pocket, and either sterically block the subsequent acetylation reaction or react with the oxocarbenium ion intermediate may act as effective Sir2-specific inhibitors, while compounds that cannot react with the reaction intermediate and do not perturb the acetylation reaction, would function as Sir2 activators by alleviating nicotinamide inhibition. Since endogenous levels of nicotinamide limit Sir2 activity in yeast cells (Sauve, et al. (2005) *Mol. Cell* 17:595-601), relief of nicotinamide inhibition is a physiologically viable approach to Sir2 activation.

In this regard, the present invention is a method for identifying a compound which modulates the activity of a silent information regulator 2 (Sir2) protein. The method of the present invention involves designing or screening for a compound which binds to at least one amino acid residue of the nicotinamide inhibition and base exchange site of Sir2 and testing the designed or screened compound for its ability to modulate the activity of the Sir2 protein. The method of the present invention can be carried out using various in silico, in vitro or in vivo assays based on detecting interactions between the nicotinamide inhibition and base exchange site and a test compound.

Compound designed or screened in accordance with the present invention can interact with at least one of the amino acid residues of the nicotinamide inhibition and base exchange site of Sir2 (see Table 1) via various heterogeneous interactions including, but not limited to van der Waals contacts, hydrogen bonding, ionic interactions, polar contacts, or combinations thereof to contribute to the energy of binding. In general, it is desirable that the compound interacts with 2, 3, 4, 5, or 6 of the amino acid residues of the nicotinamide inhibition and base exchange site of Sir2 to enhance the specificity of the compound for one or more Sir2 proteins. In particular embodiments, the compound interacts with amino acid residue 44, 64, 67, 116, 117 or 184 of SEQ ID NO:1.

In accordance with the present invention, molecular design techniques can be employed to design, identify and synthesize chemical entities and compounds, including inhibitory and stimulatory compounds, capable of binding to the nicotinamide inhibition and base exchange site of Sir2 proteins. The structure of the nicotinamide inhibition and base exchange site of Sir2 can be used in conjunction with computer modeling using a docking program such as GRAM, DOCK, HOOK or AUTODOCK (Dunbrack, et al. (1997) *Folding & Design* 2:27-42) to identify potential modulators of Sir2 proteins (e.g., yHst2, human SirT1 or human SirT2). This procedure can include computer fitting of compounds to the nicotinamide inhibition and base exchange site of Sir2 to ascertain how well the shape and the chemical structure of the compound will complement the nicotinamide inhibition and base exchange site or to compare the compound with the binding of nicotinamide in the nicotinamide inhibition and base exchange site. Computer programs can also be employed to estimate the attraction, repulsion and stearic hindrance of the Sir2 protein and effector compound. Generally, the tighter the fit, the lower the stearic hindrances, the greater the attractive forces, and the greater the specificity which are important features for a specific effector compound which is more likely to interact with Sir2 proteins rather than other classes of proteins.

Alternatively, a chemical-probe approach can be employed in the design of Sir2 modulators. For example, Goodford ((1985) *J. Med. Chem.* 28:849) describes several commercial software packages, such as GRID (Molecular Discovery Ltd., Oxford, UK), which probe the nicotinamide inhibition and base exchange site of Sir2 with different chemical probes, e.g., water, a methyl group, an amine nitrogen, a carboxyl oxygen, and a hydroxyl. Favored sites for interaction between the nicotinamide inhibition and base exchange site and each probe are thus determined, and from the resulting three-dimensional pattern of such sites a putative complementary molecule can be generated.

The compounds of the present invention can also be designed by visually inspecting the three-dimensional structure of Sir2 to determine more effective inhibitors or activators. This type of modeling is generally referred to as "manual" drug design. Manual drug design can employ visual inspection and analysis using a graphics visualization program such as "O" (Jones, et al. (1991) *Acta Crystallographica Section A* A47:110-119).

Initially effector compounds can be selected for their structural similarity to the X, Y and Z constituents of, e.g., nicotinamide by manual drug design. The structural analog thus designed can then be modified by computer modeling programs to better define the most likely effective candidates. Reduction of the number of potential candidates is useful as it may not be possible to synthesize and screen a countless number of compound variations that may have some similarity to known inhibitory molecules. Such analysis has been shown effective in the development of HIV protease inhibitors (Lam, et al. (1994) *Science* 263:380-384; Wlodawer, et al. (1993) *Ann. Rev. Biochem.* 62:543-585; Appelt (1993) *Perspectives in Drug Discovery and Design* 1:23-48; Erickson (1993) *Perspectives in Drug Discovery and Design* 1:109-128). Alternatively, random screening of a small molecule library could lead to modulators whose activity may then be analyzed by computer modeling as described above to better determine their effectiveness as inhibitors or activators.

Programs suitable for searching three-dimensional databases include MACCS-3D and ISIS/3D (Molecular Design Ltd, San Leandro, Calif.), ChemDBS-3D (Chemical Design Ltd., Oxford, UK), and Sybyl/3 DB Unity (Tripos Associates, St Louis, Mo.). Programs suitable for compound selection and design include, e.g., DISCO (Abbott Laboratories, Abbott Park, Ill.), Catalyst (Bio-CAD Corp., Mountain View, Calif.), and ChemDBS-3D (Chemical Design Ltd., Oxford, UK).

The compounds designed using the information of the present invention can bind to all or a portion of the nicotinamide inhibition and base exchange site of Sir2 and may be more potent, more specific, less toxic and more effective than known inhibitors for Sir2 proteins. The designed compounds can also be less potent but have a longer half-life in vivo and/or in vitro and therefore be more effective at modulating Sir2 protein activity in vivo and/or in vitro for prolonged periods of time. Such designed modulators are useful to inhibit or activate Sir2 protein activity to, e.g., alter p53 activity, apoptosis, lifespan or sensitivity of cells or organisms to stress.

The present invention also provides the use of molecular design techniques to computationally screen small molecule databases for chemical entities or compounds that can bind to Sir2 in a manner analogous to the nicotinamide as defined by the structure of the present invention. Such computational screening can identify various groups which interact with one or more amino acid residues of the nicotinamide inhibition and base exchange site of Sir2 and can be employed to synthesize the modulators of the present invention.

Based upon the identification of the nicotinamide inhibition and base exchange site of Sir2, in vitro (i.e., in solution) screening assays can also be carried out to identify compounds which selectively bind at the nicotinamide inhibition and base exchange site of Sir2 and inhibit or activate Sir2 protein activity. Selective binding of an agent to the nicotinamide inhibition and base exchange site of Sir2 is achieved by combining a Sir2 protein with $NAD^+$, an acetyl-lysine substrate and nicotinamide in solution and determining whether a test compound can either sterically block the subsequent acetylation reaction, react with $NAD^+$ or a reaction intermediate, or displace or alleviate nicotinamide inhibition.

Compounds which can be screened in accordance with the method of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. Databases of chemical structures are also available from a number of sources including Cambridge Crystallographic Data Centre (Cambridge, UK) and Chemical Abstracts Service (Columbus, Ohio). De novo design programs include Ludi (Biosym Technologies Inc., San Diego, Calif.), Sybyl (Tripos Associates) and Aladdin (Daylight Chemical Information Systems, Irvine, Calif.).

Library screening can be performed as disclosed herein and can be performed in any format that allows rapid preparation and processing of multiple reactions. For in vitro screening assays, stock solutions of the test compounds as well as assay components can be prepared manually and all subsequent pipeting, diluting, mixing, washing, incubating, sample readout and data collecting carried out using commercially available robotic pipeting equipment, automated work stations, and analytical instruments for detecting the signal generated by the assay. Examples of such detectors include, but are not limited to, luminometers, spectrophotometers, and fluorimeters, and devices that measure the decay of radioisotopes.

After designing or screening for a compound which binds to at least one amino acid residue of the nicotinamide inhibition and base exchange site of Sir2, the compound is subsequently tested for its ability to modulate the activity of the Sir2 protein. Such testing can be based upon whether the compound modulates the deacetylase activity of Sir2 (e.g., in a histone deacetylase assay), nicotinamide exchange activity, or based on binding activity. To measure binding constants (e.g., $K_d$), any suitable method known to those in the art can be employed including, e.g., BIACORE analysis, isothermal titration calorimetry, ELISA with a known drug on the plate to show competitive binding, or by a deacetylase activity assay. Alternatively, the compound can be co-crystallized with Sir2 to determine the binding characteristics through X-ray crystallography techniques. See, for example, U.S. Pat. No. 7,149,280 which discloses a method for identifying a ligand of a target macromolecule by obtaining an X-ray crystal diffraction pattern of a compound bound to the macromolecule crystal.

To further evaluate the efficacy of a compound identified using the method of the invention, one of skill will appreciate that a model system of any particular disease or disorder involving Sir2 proteins can be utilized to evaluate the adsorption, distribution, metabolism and excretion of a compound as well as its potential toxicity in acute, sub-chronic and chronic studies. For example, the effector or modulatory compound can be tested in an assay for replicative lifespan in *Saccharomyces cerevisiae* (Jarolim, et al. (2004) *FEMS Yeast Res.* 5(2):169-77) or for the ability to modulate the health and survival of mice on a high-calorie diet (Baur, et al. (2006) *Nature* 444(7117):337-42). See also assays disclosed in U.S. Patent Application No. 20060025337.

By way of illustration of the instant screening method, libraries of compounds were screened in vitro to identify compounds which relieved nicotinamide inhibition of Sir2 (i.e., Sir2 activators), as well as compounds which inhibited Sir2 activity. Screening assays identified the activators listed in Table 2 and inhibitors listed in Table 3.

TABLE 2

| Chemical Name | Structure | Fold Activation |
| --- | --- | --- |
| 9-(3-Fluorophenyl)-3,3,6,6-tetramethyl-2,4,6,7,9,10-hexahydro-2H,5H-acridine-1,8-dione | 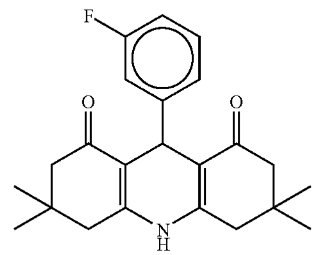 | 2.2 |
| 6-(4-Fluorophenyl)-2,3-diphenyl-1,5-dihydro-imidazo[1,2-a]imidazole | | 2.9 |

TABLE 3

| Chemical Name | Structure | $IC_{50}$ (μM) |
| --- | --- | --- |
| Cadmium acetate | 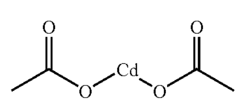 | 1.0 ± 1.2 |
| Zinc pyrithione | 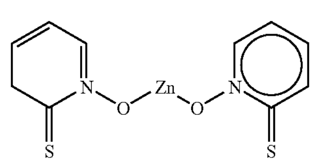 | 1.8 ± 1.3 |
| Hexachlorophene | 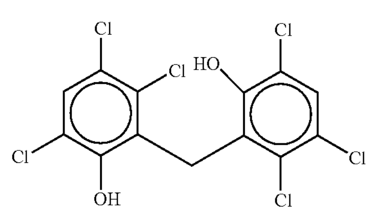 | 10.9 ± 1.5 |

TABLE 3-continued

| Chemical Name | Structure | IC$_{50}$ (µM) |
|---|---|---|
| 7-48 | 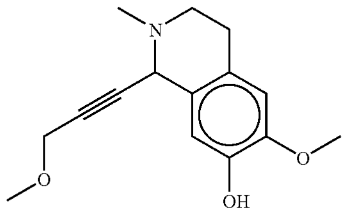 | 80.0 ± 1.4 |
| 7-47 | 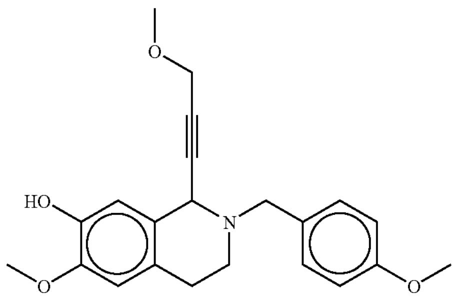 | 135.8 ± 1.3 |
| 3-(4-Allylidene-3-methylene-2-oxo-pyrrolidin-1-yl)-propionic acid | | 19.8 ± 1.1 |
| 4-(4-Ethyl-phenoxy-butyric acid 6-oxo-5λ$^3$, 6λ- benzo[c]chromen-3-yl este | 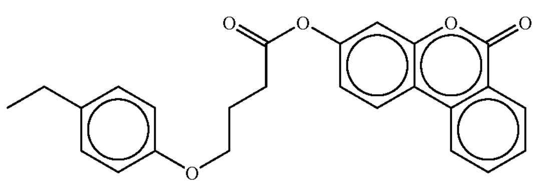 | 6.0 ± 1.2 |

The compounds identified in accordance with the present screening assay can be used as is or, as is conventional in the art, used as lead compounds to identify additional, structurally related compounds or derivatives which activate or inhibit Sir2. For example, the instant compounds can be modified to include additional substituents (e.g., O, N, S, OH, CH$_3$, halo groups, phenyl groups, alkyl groups, etc.), remove substituents (e.g., O, N, S, OH, CH$_3$, halo groups, phenyl groups, alkyl groups, etc.), or substitute groups (e.g., substitute one halo group for another) in order to provide compounds with improved activity and/or efficacy. As with the initial screens, modified compounds or compound derivatives can be screened via in silico, in vitro, or in vivo methods to determine activity.

Compounds which bind to at least one amino acid residue of the nicotinamide inhibition and base exchange site of Sir2 can be used in a method for modulating (i.e., blocking or inhibiting, or enhancing or activating) a Sir2 protein. Such a method involves contacting a Sir2 protein either in vitro or in vivo with an effective amount of a compound that interacts with at least one amino acid residue of the nicotinamide inhibition and base exchange site of Sir2 so that the activity of the Sir2 protein is modulated. An effective amount of an effector or modulatory compound is an amount which reduces or increases the activity of the Sir2 protein by 10%, 20%, 30%, 40%, 50%, 60%, 70%, 80%, 90% or 100%. Such activity can be monitored by enzymatic assays detecting activity of the Sir2 protein or by monitoring the expression or activity of proteins which are known to be regulated by Sir2 protein (e.g., hTERT, p53, PML, BCL6, TAF$_1$68, or CTIP2)

As will be appreciated by one of skill in the art, modulating the activity of a Sir2 protein can be useful in selectively analyzing Sir2 protein signaling events in model systems as well as in preventing or treating diseases and disorders involving Sir2 protein. For example, human SirT1 is involved in muscle differentiation, apoptosis, and neurodeneration and therefore a compound which activates SirT1 will be useful in the prevention or treatment of neurodegenerative diseases such as Alzheimer's disease, amyotrophic lateral sclerosis (ALS), Parkinson's disease, Huntington's disease, and multiple sclerosis.

Sir2 is also involved in senescence, lifespan, and cell proliferation. In this regard, Sir2-activating compounds can be used in methods for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. Moreover, Sir2 protein effectors can be used in the treatment of diabetes, obesity, and cancer.

Prevention or treatment typically involves administering to a subject in need of treatment a pharmaceutical composition containing an effective of a compound identified in the screening method of the invention. In most cases this will be a human being, but treatment of agricultural animals, e.g., livestock and poultry, and companion animals, e.g., dogs, cats and horses, is expressly covered herein. The selection of the dosage or effective amount of a compound is that which has the desired outcome of preventing, reducing or reversing at least one sign or symptom of the disease or disorder being treated. Such signs or symptoms are well-known in the art and can be monitored by the skilled clinician upon commencement of treatment.

Pharmaceutical compositions can be in the form of pharmaceutically acceptable salts and complexes and can be provided in a pharmaceutically acceptable carrier and at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the subject being treated.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

The invention is described in greater detail by the following non-limiting examples.

EXAMPLE 1

Materials and Methods

Protein Preparation, Crystallization and Structure Determination. The 64-residue C-terminal deletion construct of yHst2 (residues 1-294) and point mutants were purified and expressed according to established methods (Zhao, et al. (2003) *Nat. Struct. Biol.* 10:864-871). Point mutations in yHst2 (1-294) were generated from the pRSET-A plasmid overexpressing the N-terminal $His_6$-tagged fusion protein with site-directed mutagenesis based on the QUIKCHANGE protocol from STRATAGENE (Papworth, et al. (1996) *Strategies* 9:3-4).

Crystals of the yHst2/ADP-HPD/H4 and the yHst2 I117F/carba-$NAD^+$/H4 complexes were grown using the vapor diffusion method at room temperature and were obtained by equilibrating about 0.15 mM of the respective complex against a reservoir solution containing 2.0 M $(NH_4)_2SO_4$, 100 mM Na citrate, pH 5.6, 200 mM K/Na tartrate or 2.0 M $(NH_4)_2SO_4$ and 100 mM Na citrate, pH 5.5. To obtain nicotinamide bound complex, yHst2/ADP-HPD/H4 crystals were soaked with reservoir solution supplemented with 50 mM nicotinamide. All crystals were flash frozen in reservoir solution supplemented with 25% (vol/vol) glycerol for data collection.

All crystallographic data was collected on the A1 beamline at CHESS, and processed with the HKL2000 suite (HKL Research, Charlottesville, Va.). The structures were solved with the program AMoRe (Navaza (1994) *Acta Crystallographica Section A* A50:157-163) using the yHst2/ADP-ribose/H4 structure (PDB code 1SZD) as a molecular replacement model for the yHst2/ADP-HPD/H4 and yHst2/ADP-HPD/H4+nicotinamide complex structures and the yHst2/carba-$NAD^+$/H4 structure (PDB code 1SZC) as a molecular replacement model for the yHst2 1117F/carba-$NAD^+$/H4 complex structure. Structures were refined with CNS (Brunger, et al. (1998) *Acta Crystallogr. D Biol. Crystallogr.* 54:905-921) with model building with O (Jones, et al. (1991) supra) with the nicotinamide built into IFo-Fc difference density of the yHst2/ADP-HPD/H4+nicotinamide structure at the end of the refinement. The final models were checked with composite-simulated annealing omit maps.

Kinetic Assays. All enzymatic assays were carried out at room temperature in a buffer containing 25 mM Tris-HCl, pH 8.0, 137 mM NaCl, 2.7 mM KCl, and 1 mM $MgCl$ using a deacetylase fluorescent activity assay kit (AK-555, Biomol Research Laboratories, Plymouth Meeting, Pa.). One μM protein, and 500 μM of both $NAD^+$ and fluorogenic acetyl-lysine substrate were used and reactions were quenched after 15 minutes by the addition of 10 mM nicotinamide inhibitor and fluorogenic-lysine developer. For $NAD^+$ $K_m$ measurements, 1 μM protein, saturating fluorogenic acetyl-lysine substrate (100 μM), and varying concentrations of $NAD^+$ (0.5-

5000 μM) were used. Data taken in triplicate were fitted to the equation $1/v=(K_m/V_{max})(1/[S])+1/V_{max}$, using a root mean least squares approach in the form of a double reciprocal Lineweaver-Burk plot where the x-intercept is equal to $-1/K_m$. For nicotinamide $K_i$ measurements, 1 μM protein, saturating fluorogenic acetyl-lysine substrate (100 μM) and varying amounts of NAD⁺ (5-2000 μM) and nicotinamide (0-1 mM) were used. Data taken in triplicate were fitted to the equation $1/v=(1+K_m/[S])/V_{max}K_{ii}*[I]+1/V_{max}(1+K_m/[S])$, using a root mean least squares approach in the form of a Dixon plot for a strict noncompetitive inhibitor where $K_{ii}$ is equal to −x at the −x intercept. The slopes of the Dixon Plot were replotted versus 1/[NAD⁺], and the slope of the corresponding line was set equal to $K_m/(V_{max}*K_i)$, in order to calculate $K_i$.

EXAMPLE 2

Structure of Nicotinamide Bound to an yHst2/Acetyllysine/ADP-HPD Ternary Complex The structure of a ternary complex of yHst2 bound to an acetyl-lysine 16 histone H4 derived peptide and carba-NAD⁺, a non-hydrolysable NAD⁺ analogue (Slama and Simmons (1988) *Biochemistry* 27:183-193; Slama and Simmons (1989) *Biochemistry* 28:7688-7694; Zhao, et al. (2004) supra) has been reported. The structure revealed that the acetyl group of the acetyl-lysine substrate hydrogen bonds to the 2' and 3' hydroxyl groups of the cyclopentane ring, presumably to help position the nicotinamide group in the highly conserved C pocket for hydrolysis, leaving the acetyl group inappropriately positioned for nucleophilic attack of the 1' carbon. A comparison of this structure with a ternary complex in which ADP-ribose replaces carba-NAD⁺, reveals that the ribose ring is rotated by about 90° relative to its corresponding position in carba-NAD⁺ with the 1'-hydroxyl group of the ADP-ribose ring pointing into another highly conserved, hydrophobic "D pocket" that could accommodate an incoming nicotinamide group for a transglycosidation reaction to reform β-NAD⁺ (Zhao, et al. (2004) supra).

To trap free nicotinamide bound to a relevant sirtuin complex, crystals of a ternary complex containing yHst2, an acetyl-lysine 16 histone H4 peptide and the intermediate analogue ADP-HPD were prepared, and soaked crystals with high concentrations of nicotinamide. ADP-HPD was selected as an intermediate analogue for these studies because of its similarity to the proposed positively charged oxocarbenium ion reaction intermediate that is expected to form directly after cleavage of the glycosidic bond between nicotinamide and ADP-ribose (Slama, et al. (1995) *J. Med. Chem.* 38:389-393).

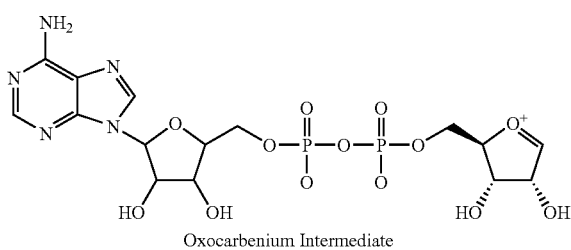
Oxocarbenium Intermediate

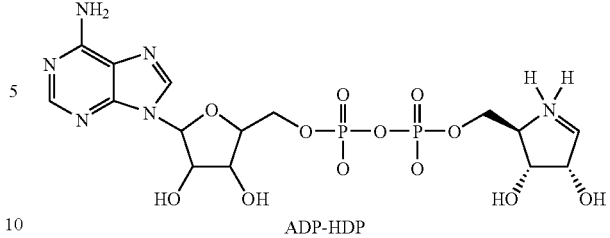
ADP-HDP

Crystals of the ternary yHst2/ADP-HPD/histone H4 complex in the presence and absence of nicotinamide were isomorphous to the previously described yeast Hst2/ADP-ribose/histone H4 crystals (Zhao, et al. (2004) supra) and formed in the space group P3₂21 containing one molecule per asymmetric unit. The structures were determined by molecular replacement and refined to resolutions of 2.05 Å and 2.00 Å, respectively (Table 4).

TABLE 4

|  | yHst2/ADP-HPD/H4 | yHst2/ADP-HPD/H4 + nicotinamide | yHst2 I117F/carba-NAD⁺/H4 |
|---|---|---|---|
| Data Collection |  |  |  |
| Space Group | P3₂21 | P3₂21 | P3₂21 |
| Cell parameters, Å | a = b = 106.76, c = 67.7 | a = b = 105.94, c = 67.1 | a = b = 106.65, c = 67.7 |
| Resolution, Å | 50-2.00 | 50-2.05 | 50-2.07 |
| Unique reflections | 28626 | 27580 | 25169 |
| Completeness, %* | 94.2 (94.0) | 99.9 (99.6) | 91.9 (94.5) |
| Multiplicity* | 6.5 (6.1) | 6.1 (5.8) | 6.0 (5.9) |
| I/σ. | 53.3 (6.6) | 20.0 (5.6) | 31.5 (10.6) |
| Rmerge, %*† | 6.4 (39.6) | 11.1 (32.0) | 4.6 (11.3) |
| Refinement Statistics |  |  |  |
| Rwork, %‡ | 22.5 | 21.9 | 22.5 |
| Rfree, %§ | 23.3 | 24.6 | 23.3 |
| Number of atoms |  |  |  |
| Protein# | 2312 | 2286 | 2313 |
| H4 peptide | 56 | 61 | 56 |
| Carba-NAD⁺# |  |  | 44 |
| ADP-HPD | 35 | 35 |  |
| Nicotinamide |  | 9 |  |
| Water | 116 | 133 | 180 |
| Zn ions# | 1 | 1 | 1 |
| Rms deviations |  |  |  |
| Bond length, Å | 0.007 | 0.006 | 0.007 |
| Bond angles, ° | 1.2 | 1.2 | 1.3 |
| Bfactors, Å² | 34.5 | 36.9 | 41.5 |

*Values in parentheses are from the highest resolution shell.
Values for each molecule in the asymmetric unit.
†$R_{merge} = \Sigma|i - <I>|/\Sigma<>$.
‡$R_{working} = \Sigma||F_O| - |F_C||/\Sigma|F_O|$.
§$R_{free} = \Sigma_T||F_O| - |F_C||/\Sigma_T^b|F_O|$, where T is a test set of a percentage (5% for all structures) of the total reflections randomly chosen and set aside before refinement.

The structure of the nicotinamide-bound and free complexes were very similar to each other, with an rms deviation of 0.235 Å for $C_\alpha$ atoms and the acetyl-lysine and ADP-HPD ligands were also almost identical between these two structures and the previously described ADP-ribose containing complex. The ribose-ring mimic of ADP-HPD was bound in a largely hydrophobic pocket and made only one polar interaction in which a network of water molecules bridged a hydrogen bond between the ring nitrogen of ADP-HPD and N116.

EXAMPLE 3

The Nicotinamide Binding Site

The most significant difference between the nicotinamide-bound and free complexes was the presence of a nicotinamide molecule bound in the highly conserved D pocket, adjacent to the β-face of the ADP-HPD molecule in the nicotinamide-bound complex. This pocket was distinct from the C pocket of the nicotinamide moiety of the substrate NAD⁺. It was mostly hydrophobic and formed by residues E64, F184, and F67 around the pyridine ring, and F44 and I117 proximal to the carboxyamide moiety. Of the residues that formed pocket D, F44, F67, N116 and F184 were strictly conserved, and E64 and I117 were only conservatively substituted, indicating that this binding site is important for nicotinamide regulation of Sir2 proteins. Since ADP-HPD is analogous to the proposed oxocarbenium intermediate, this conformation of bound nicotinamide is consistent with a nicotinamide molecule binding to the protein complex after the initial nicotinamide cleavage and reacting with the oxocarbenium intermediate, reforming β-NAD⁺. Importantly, the conformation of nicotinamide as described would only be consistent with the exclusive formation of β-NAD⁺.

The nicotinamide molecule had a slightly higher B factor, 74 Å², than the average B factor for the protein atoms in that complex, and the density for the carboxyamide better defined than for the pyridine ring, indicating greater flexibility of the pyridine ring. The carboxyamide oxygen of nicotinamide made a water-mediated hydrogen bond to the backbone nitrogen of I117, while the carboxyamide nitrogen made water-mediated hydrogen bonds to the backbone nitrogen of I117, and the sidechain carbonyl oxygen of N116 and a phosphate oxygen of the ADP-HPD ligand. The pyridine ring of the nicotinamide molecule also made van der Waals interactions with F44 and F67. Residues F44, F67, N116, and I117 are strictly conserved across Sir2 homologues, highlighting the significance of these interactions. Since the nicotinamide pyridine ring makes exclusively van der Waals interactions in the binding pocket and the density for this region is not as clear as for the carboxyamide moiety of nicotinamide, it is contemplated that the ring is free to rotate in the binding pocket. It is believed that when acetyl-lysine is bound, the pyridine ring flips away from the acetyl group and toward the β face of the ribose ring where it can carry out nucleophilic attach of the 1β carbon of the ribose ring of the oxocarbenium ion intermediate. The kinetics of both the cleavage of nicotinamide from NAD⁺ to form the oxocarbenium intermediate, and the attack of the 2'-OH on the acetyl carbonyl carbon are fast as compared to the overall reaction rate (Smith and Denu (2006) *Biochemistry* 45:272-282). Although enzyme where the general base, R135, is mutated to alanine accumulates the α-1'-O-alkylamidate intermediate, wild-type enzyme accumulates neither the α-1'-O-alkylamidate intermediate or the oxocarbenium intermediate (Smith and Denu (2006) supra), indicating that the presence of nicotinamide in its binding site when or immediately after the intermediate forms will determine whether base exchange or deacetylation chemistry will occur. The structure disclosed herein clearly shows that both nicotinamide and the oxocarbenium intermediate are capable of binding simultaneously to the enzyme active site in a conformation suitable for base exchange chemistry.

In order for nicotinamide to bind the enzyme/oxocarbenium/acetyl-lysine complex, there must be a tunnel that leads from the enzyme active site to solvent in this complex. Indeed, in the nicotinamide bound complex there was a hydrophobic tunnel from the nicotinamide binding site to bulk solvent. The tunnel was formed by residues 37-43 of the flexible β1-α2 loop and was approximately 9×8 Å in diameter, a sufficient size to accommodate a nicotinamide molecule. In the nicotinamide bound complex, the tunnel was occupied by a number of water molecules that made hydrogen bonds mainly to backbone atoms. It is contemplated that after cleavage of NAD⁺ and the formation of the oxocarbenium intermediate, nicotinamide diffuses from solvent or the C pocket through this hydrophobic tunnel to the enzyme active site where it participates in base exchange. This is supported by a superposition of residues that form this tunnel in a number of yHst2 complexes, as substrate or intermediate ternary complexes show an open conformation that would allow nicotinamide to diffuse out or into the tunnel, respectively, while, binary or product complexes show a more closed tunnel.

EXAMPLE 4

Mutations that Affect Nicotinamide Inhibition

Figure 1B:
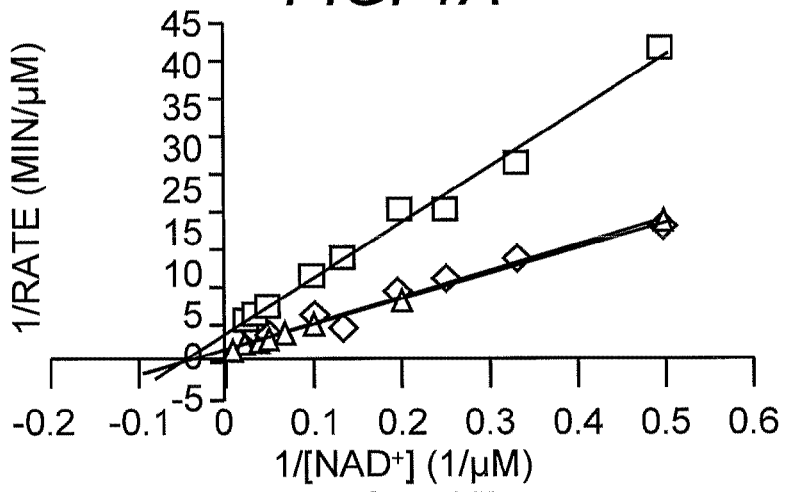
FIG. 1B is a Lineweaver-Burk plot describing the NAD$^+$ binding kinetics of wild-type yHst2 (diamonds), the yHst2 I117F and I117V mutants (squares and triangles, respectively) done in triplicate.

The sidechain of residue I117 sits in the back of the hydrophobic D pocket to which nicotinamide is bound in the yHst2/ADP-HPD/histone H4 nicotinamide bound complex structure, and participates in van der Waals interactions with nicotinamide. To further probe the physiological relevance of this free nicotinamide binding site, yHst2 residue I117 was mutated to several residues and the effect of these mutations on nicotinamide inhibition was measured. Mutations to very large (Y, W), small (A), or charged (H, D) residues rendered the enzyme nearly or completely catalytically inactive, while the mutations I117V or I117F were nearly as active as the wild-type protein (FIG. 1A). Bisubstrate kinetic analysis of the I117V or I117F mutants revealed that they had slightly higher $K_m$ values for NAD⁺ relative to the wild-type enzyme, 25.5 μM, 25.8 μM, and 16.1 μM, respectively (FIG. 1B).

Figure 1C:
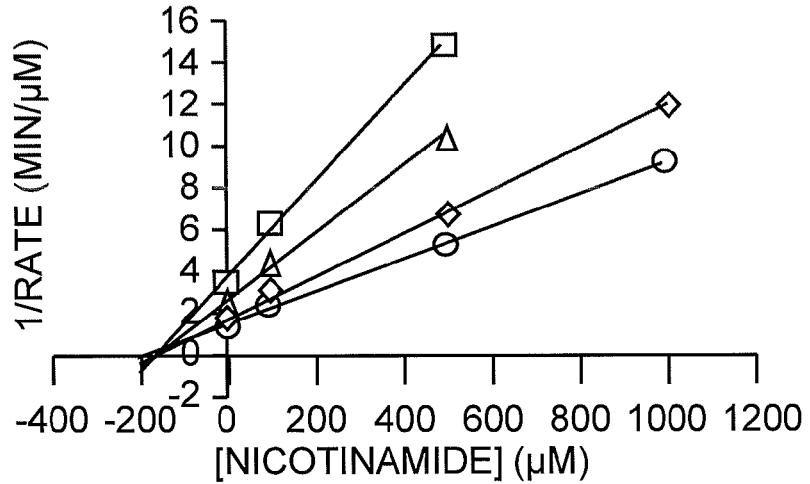
FIG. 1C is a Dixon plot describing the nicotinamide inhibition of wild-type yHst2 at varying concentrations of NAD$^+$, 15 μM (squares), 25 μM (triangles), 50 μM (diamonds), and 80 μM (circles). Each line is fit to an equation for a noncompetitive inhibitor with data obtained in triplicate.
Figure 1D:
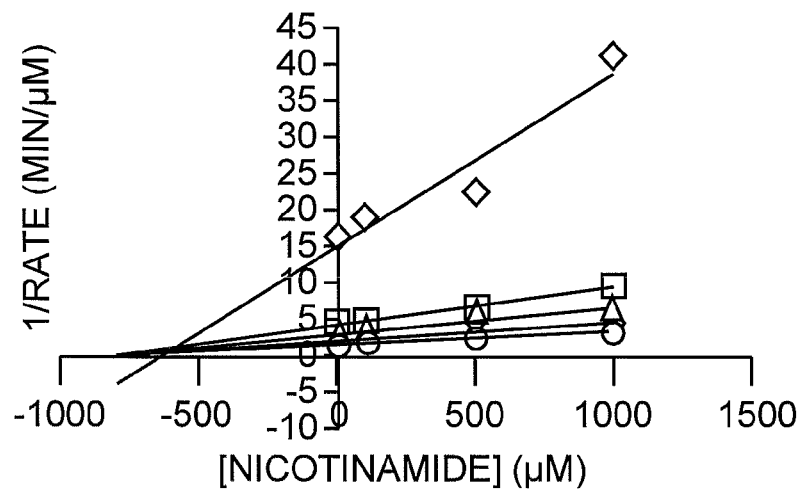
FIG. 1D is a Dixon plot describing the nicotinamide inhibition of yHst2 I117F with conditions as described in FIG. 1C, but also including 5 μM NAD$^+$ (diamonds).
Figure 1E:
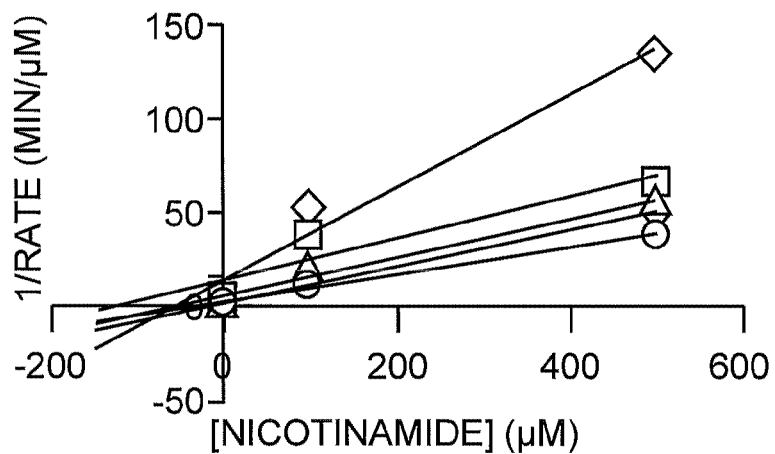
FIG. 1E is a Dixon plot describing the nicotinamide inhibition of yHst2 I117V with conditions as described in FIG. 1D.

Since the I117V and I117F yHst2 mutations had near wild-type activity for deacetylation, their ability to be inhibited by nicotinamide was compared. The $K_{ii}$ for nicotinamide was 1000±30 μM ($K_{is}$=720±40 μM) for the I117F mutant enzyme, a nearly 6-fold increase over the $K_{ii}$ for nicotinamide of wild-type enzyme, 170±28 μM ($K_{is}$=140±3 μM) (FIGS. 1C and 1D). This finding is consistent with the bulkier phenylalanine residue partially occluding the nicotinamide binding site within the D pocket. Notably, this increase is much larger than would be expected if free nicotinamide bound in the C pocket because the increased $K_m$ for NAD⁺ is less than 2-fold for the I117F mutant enzyme as compared to the wild-type enzyme. Conversely, the $K_{ii}$ for nicotinamide was 65±40 μM ($K_{is}$=65±1.1 μM) for the I117V mutant enzyme (FIG. 1E), a nearly 2.5-fold decrease over the $K_{ii}$ for nicotinamide of the wild-type enzyme. This result is also consistent with valine being a smaller residue that slightly expands the D pocket, therefore making this pocket slightly more sensitive to nicotinamide inhibition. Together, these functional studies indicate that the D pocket disclosed herein is the site for nicotinamide inhibition.

Figure 1F:
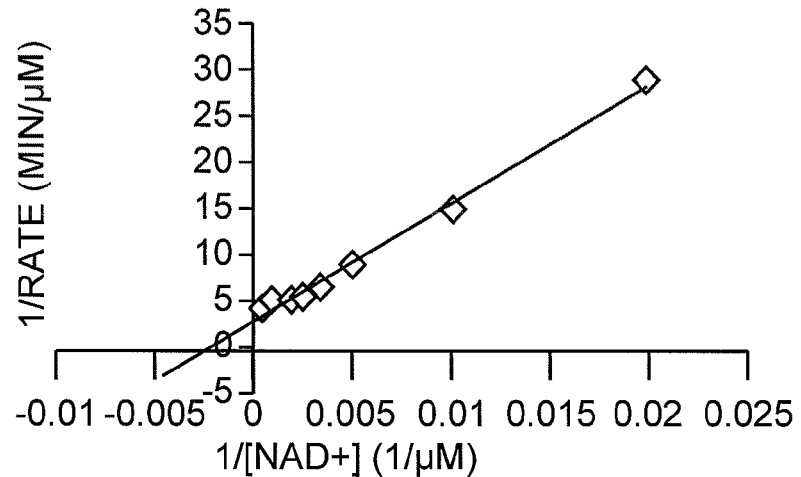
FIG. 1F is a Lineweaver-Burk plot describing the NAD$^+$ binding kinetics of yHst2 D118N (diamonds) with data obtained in triplicate.
Figure 1G:
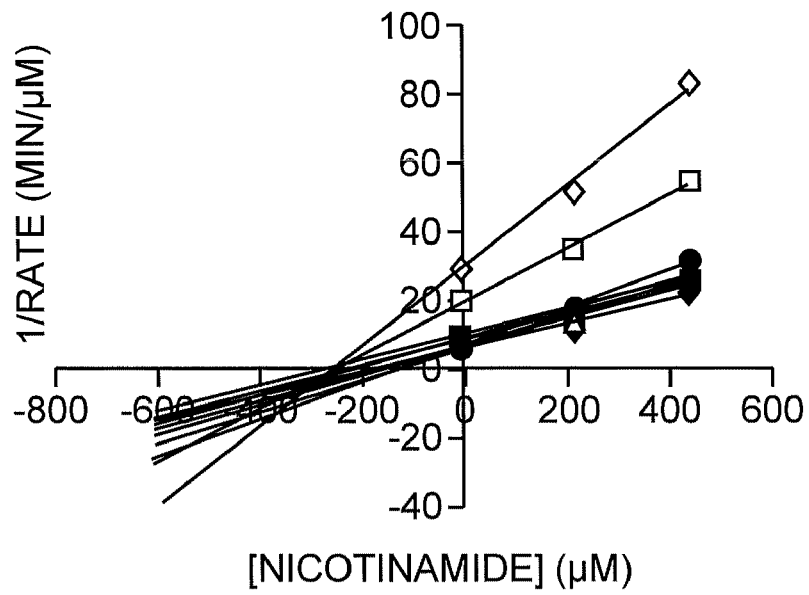
FIG. 1G is a Dixon plot describing the nicotinamide inhibition of yHst2 D18N at varying concentrations of NAD$^+$, 50 μM (open diamonds), 100 μM (open squares), 250 μM (solid squares), 450 μM (solid diamonds), 600 μM (open circles), 800 μM (solid circles), 1000 μM (minus signs), 1250 μM (open triangles), 1500 μM (plus signs), 2000 μM (solid triangles).

Nicotinamide has also been shown to inhibit Sir2 enzymes through the same binding pocket that binds the nicotinamide group of NAD⁺, the C pocket (Avalos, et al. (2005) supra). In this study, a D101N mutation in Sir2Tm, a Sir2 homologue from the thermaphilic bacterium *Thermotoga maritima*, resulted in an enzyme that was significantly compromised for both NAD⁺ binding and sensitivity to nicotinamide inhibition. The native aspartic acid residue participates in hydrogen bonding interactions with the amide group of the nicotinamide moiety of NAD⁺, an interaction that is also observed via the corresponding aspartic acid 118 of yHst2 in the yHst2/carba-NAD$^+$/acetyl-lysine histone H4 complex. To address the significance of the C pocket in nicotinamide inhibition of yHst2, the corresponding D118N mutation in yHst2 was prepared and its enzymatic properties were characterized. As illustrated in FIG. 1A, the D118N mutant retained approximately 13% of the activity of the wild-type protein, with an apparent $K_m$ for NAD$^+$ of 453.5 µM, a more than 28-fold increase over the wild-type $K_m$ for NAD$^+$ (FIGS. 1B and 1F). This increase in $K_m$ for NAD$^+$ was because the substitution of aspartic acid with asparagine disrupts the important hydrogen bond between the amide group of NAD$^+$ and the Asp118 side chain. Subsequently, the $K_{ii}$ for nicotinamide of the D118N mutant was measured. The $K_{ii}$ for nicotinamide for D118N was 180±50 µM ($K_i$=320±30 µM) (FIG. 1G), very similar to the wild-type value of 170±28 µM. This result indicates that a yHst2, mutation of the C pocket residue, Asn118, has a negligible effect on the sensitivity of the enzyme to nicotinamide inhibition, leading to the conclusion that the D pocket plays a more significant role that the C pocket for nicotinamide inhibition of yHst2 and likely other eukaryotic deacetylases.

EXAMPLE 5

Structure of yHst2 I117F in Ternary Complex with Acetyl-Lysine 16 Histone H4 and Carba-NAD$^+$ To demonstrate that the sidechain of residue 117 occupies the free nicotinamide binding site, pocket D, and when mutated to phenylalanine, occludes a physiologically relevant nicotinamide binding site, the structure of yHst2 I117F bound to an acetylated histone H4-derived peptide and carba-NAD$^+$ was determined. This complex was isomorphous to the previously described wild-type complex (Zhao, et al. (2004) supra) and to the ADP-HPD containing yHst2 complexes described herein. The structure was solved by molecular replacement and refined to 2.0 Å (Table 4).

The yHst2 I117F complex superimposed very well with the wild-type complex. Notably, the hydrogen bonding distance between the carboxyamide carbonyl oxygen of carba-NAD$^+$ and the backbone nitrogen of residue 117 was virtually identical, 2.94 Å and 2.89 Å, respectively, between the mutant complex and the wild-type complex, indicating that mutation of residue I117 had a very minor effect on NAD$^+$ binding, and would have a similarly minor effect on nicotinamide binding, if free nicotinamide bound in the site previously occupied by the nicotinamide moiety of NAD$^+$, as has been proposed (Avalos, et al. (2005) supra; Avalos, et al. (2004) supra).

The structure of the yHst2 I117F complex showed clear density for the phenylalanine side chain of residue 117 protruding into the free nicotinamide binding pocket described herein, and not into the C pocket that would be occupied by the nicotinamide moiety of NAD$^+$. The phenylalanine side chain did not seem to alter the conformation of the nicotinamide moiety of carba-NAD$^+$, nor disrupt the interactions this moiety made with any protein residues. Since the yHst2 I117F/carba-NAD$^+$/histone H4 complex was isomorphous with the nicotinamide bound yHst2/ADP-HPD/histone H4 complex, and their protein molecules had an rms deviation of 0.25 Å$^2$ for C$^\alpha$ atoms, the two complex structures were superimposed. A view of the nicotinamide binding site of the superimposed complexes showed that the I117F sidechain indeed protruded into the free nicotinamide binding site, pocket D, in a way that was incompatible with nicotinamide binding as it was seen in the wild-type enzyme, consistent with the accompanying structural and biochemical studies pointing to the importance of the D pocket for nicotinamide inhibition and base exchange in Sir2 enzymes.

EXAMPLE 6

Screen for Agents which Modulate Sir2

Based on the identification of the nicotinamide inhibitory and base exchange site of Sir2 deacetylase enzymes, an in silico screen (using a 100,000 compound library) was carried out to identify yHst2 effectors (potential inhibitors or activators) as well as a preliminary solution screen for yHst2 and human SIRT1 (hSIRT1) effectors. Of the in silico hits, three were confirmed to be mid-low micromolar Hst2 and SIRT1 inhibitors in vitro, with the most potent compound showing an IC$_{50}$ value of about 25 µM for both enzymes. To confirm binding of this compound, co-crystallization experiments with this inhibitor and Hst2 are conducted to provide a scaffold for the structure-based design of improved Sir2 effectors (inhibitors or activators).

In parallel to the in silico screen, a solution screen for Sir2 effectors was carried out. A library containing about 10,000 Diversity Oriented Synthesis (DOS) compounds and natural product sub-libraries of compounds was screened using both yHst2 and hSIRT1 proteins. Several potential inhibitors were identified, with the most potent inhibitors having IC$_{50}$ values of 1-10 µM.

In addition, a biased in vitro screening assay was conducted to specifically identify compounds that selectively activate Hst2 by relief of nicotinamide inhibition. This in vitro screen was carried out as follows. Thirty µL of a master mix containing 0.4 µL of 5 mM Fluor de Lys-SIRT1 deacetylase substrate (KI-177; BioMol International, Plymouth Meeting, Pa.), 3.2 µL of 1 mM NAD$^+$ (Sigma, St. Louis, Mo.), 0.052 µL of 130 mM nicotinamide (Sigma), and 26.348 µL of assay buffer (25 mM Tris-Cl, pH 8.0, 137 mM NaCl, 2.7 mM KCl, 1 mM MgCl$_2$) was added to each reaction well. To the master mix was added 100 mL of either a DMSO control or a compound from the library. To begin the reaction, 10 µL of an enzyme master mix containing 2 µM Hst2 (residues 1-294) (MW=34859.9 Da) in assay buffer was added to each reaction well. After four hours, a stop/developer solution containing 8 µL of 100 mM nicotinamide, 8 µL of 5× Fluor de Lys Developer II Concentrate (5×) (KI-176, BioMol International), and 24 µL of assay buffer was added to each reaction well. After 45 minutes, each plate was read on a fluorescence plate reader at an excitation wavelength of 360 nm and an emission wavelength of 460 nm.

Figure 2:
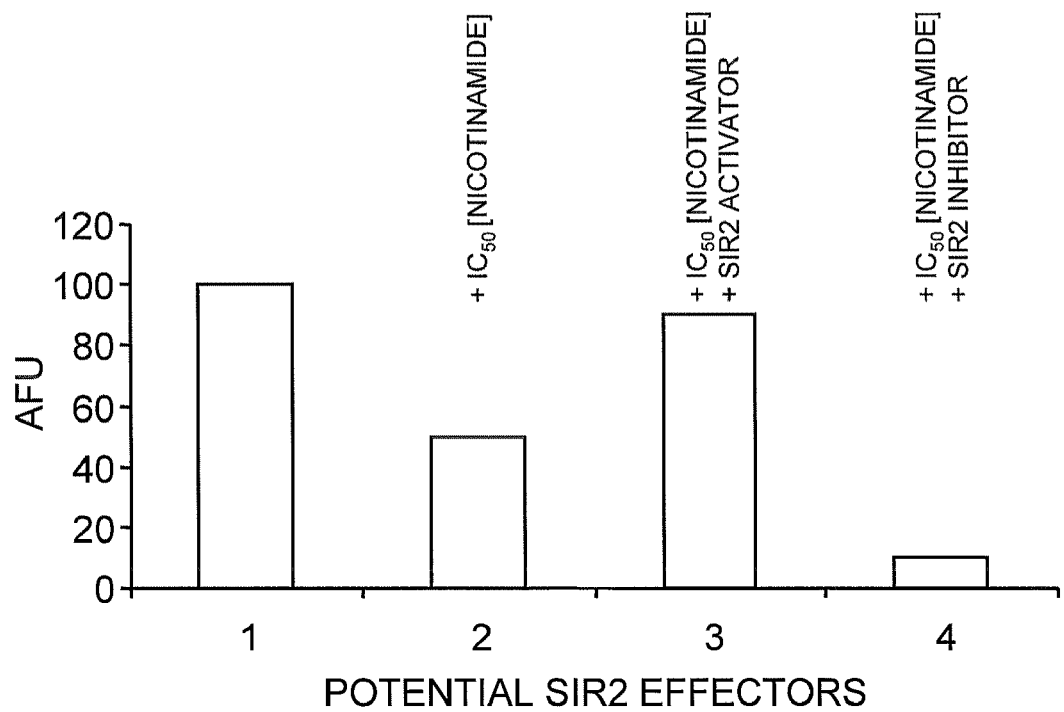
FIG. 2 shows relative fluorescent readings of reactions without (1) and with (2-4) nicotinamide in the presence of a Sir2 activator (3) or inhibitor (4).

The above-described screening assay, which contained 130 µM nicotinamide (approximately the IC$_{50}$ amount under the assay condition described above) was developed to bias the screen for selective nicotinamide antagonists. Compounds that could bind in the nicotinamide binding site of Hst2 (1-294), but still allow the deacetylase chemistry to occur, had a fluorescence reading nearly equivalent to the fluorescence reading of a reaction of the enzyme without nicotinamide present (see FIG. 2). Compounds shown in Table 2 had a Z score of ~5 and fluoresced to approximately the same level as reactions with enzyme when nicotinamide was not present. It is believed that even though nicotinamide was present in the reaction, the compound prevented nicotinamide binding, and thus relieved nicotinamide inhibition.

To confirm binding of the above-identified compounds, co-crystallization experiments with the inhibitors and Hst2 are conducted to provide a scaffold for the structure-based design of improved Sir2 effectors (inhibitors or activators).

What is claimed is:

1. A method for identifying a compound that binds to or inhibits the histone deacetylase activity of a silent information regulator 2(Sir2) protein comprising:
   a) generating on a computer a three-dimensional structure of a nicotinamide inhibition and base exchange site of a Sir2 protein of SEQ ID NO:1 in complex with nicotinamide, wherein the nicotinamide inhibition and base exchange site consists of amino acid residues 44, 64, 67, 116, 117 and 184 of SEQ ID NO:1, wherein the structural coordinates of amino acid residues 44, 64, 67, 116, 117 and 184 of SEQ ID NO:1 and nicotinamide are obtained by X-ray diffraction of a crystal of a complex of a Sir2 protein consisting of the amino acid sequence of SEQ ID NO:1 and an N-terminal hexahistidine tag, adenosine diphosphate hydroxymethyl pyrrolidinediol, an acetyl-lysine 16 histone H4 peptide, and nicotinamide, wherein the crystal has space group $P3_221$ and unit cell parameters of a=b=105.94 Å, and c=67.1 Å, and diffracts X-rays to a resolution of 2.05 Å;
   b) employing the three-dimensional structure of the nicotinamide inhibition and base exchange site to design or screen for a compound that potentially binds to said nicotinamide inhibition and base exchange site; and
   c) testing the compound designed or screened for in (b) by contacting the compound with the Sir2 protein of SEQ ID NO:1 and identifying compounds that bind to or inhibit the histone deacetylase activity of the Sir2 protein of SEQ ID NO:1.

* * * * *